US012767618B2

(12) United States Patent
Ikeda

(10) Patent No.: US 12,767,618 B2
(45) Date of Patent: Oct. 20, 2026

(54) HYDROCARBON PRODUCTION APPARATUS AND HYDROCARBON PRODUCTION METHOD

(71) Applicant: ENEOS Corporation, Tokyo (JP)

(72) Inventor: Masakazu Ikeda, Tokyo (JP)

(73) Assignee: ENEOS Corporation, Tokyo (JP)

( * ) Notice: Subject to any disclaimer, the term of this patent is extended or adjusted under 35 U.S.C. 154(b) by 472 days.

(21) Appl. No.: 18/570,917

(22) PCT Filed: Jun. 3, 2022

(86) PCT No.: PCT/JP2022/022612
§ 371 (c)(1),
(2) Date: Dec. 15, 2023

(87) PCT Pub. No.: WO2022/264836
PCT Pub. Date: Dec. 22, 2022

(65) Prior Publication Data

US 2024/0279136 A1 Aug. 22, 2024

(30) Foreign Application Priority Data

Jun. 16, 2021 (JP) ................................ 2021-100351

(51) Int. Cl.
*C07C 1/04* (2006.01)
*C01B 3/12* (2006.01)
(Continued)

(52) U.S. Cl.
CPC .............. *C07C 1/0485* (2013.01); *C01B 3/12* (2013.01); *C01B 3/38* (2013.01); *C01B 32/40* (2017.08);
(Continued)

(58) Field of Classification Search
CPC .. C01B 3/12; C01B 3/38; C01B 32/40; C01B 2203/0233; C01B 2203/0283; C01B 2203/062; C10G 2/32; C07C 1/041
See application file for complete search history.

(56) References Cited

U.S. PATENT DOCUMENTS

2010/0177861 A1 7/2010 Lecomte et al.
2011/0118366 A1 5/2011 Menzel
(Continued)

FOREIGN PATENT DOCUMENTS

EP 3670443 A1 6/2020
JP 2008248179 A 10/2008
(Continued)

OTHER PUBLICATIONS

Extended European Search Report issued on May 7, 2025, in corresponding European Patent Application No. 22824828.2. (7 pages).

(Continued)

*Primary Examiner* — Jafar F Parsa
(74) *Attorney, Agent, or Firm* — Buchanan Ingersoll & Rooney PC

(57) ABSTRACT

A hydrocarbon production apparatus includes a reverse shift reaction unit obtaining a synthesis gas by using carbon dioxide and hydrogen, a hydrocarbon production unit producing a hydrocarbon by using the synthesis gas, a gas-liquid separation unit separating a gas component containing hydrogen, carbon dioxide, and a light hydrocarbon and a liquid component containing a hydrocarbon from an effluent from the hydrocarbon production unit, a first separation unit separating hydrogen and carbon dioxide, and a light hydrocarbon from the gas component, and a catalytic reaction unit generating hydrogen and carbon monoxide by using the light hydrocarbon separated by the first separation unit. The reverse shift reaction unit also uses the hydrogen and carbon
(Continued)

dioxide separated by the first separation unit. The hydrocarbon production unit also uses the hydrogen and carbon monoxide generated by the catalytic reaction unit.

6 Claims, 6 Drawing Sheets

(51) Int. Cl.
*C01B 3/38* (2026.01)
*C01B 32/40* (2017.01)

(52) U.S. Cl.
CPC ...... *C07C 1/041* (2013.01); *C01B 2203/0233* (2013.01); *C01B 2203/0283* (2013.01); *C01B 2203/062* (2013.01); *C01B 2203/1235* (2013.01)

(56) References Cited

U.S. PATENT DOCUMENTS

| | | | |
|---|---|---|---|
| 2013/0345325 | A1 | 12/2013 | Lecomte et al. |
| 2018/0093888 | A1 | 4/2018 | Mamedov et al. |

FOREIGN PATENT DOCUMENTS

| | | | |
|---|---|---|---|
| JP | 2010-506997 | A | 3/2010 |
| JP | 2011-521089 | A | 7/2011 |
| JP | 2014517806 | A | 7/2014 |
| JP | 2022191870 | A | 12/2022 |
| WO | 2006/099573 | A1 | 9/2006 |
| WO | 2008/048414 | A1 | 4/2008 |
| WO | 2011/141635 | A1 | 11/2011 |
| WO | 2020/208008 | A1 | 10/2020 |

OTHER PUBLICATIONS

International Search Report (PCT/ISA/210) and Written Opinion (PCT/ISA/237) both with English translation mailed on Aug. 9, 2022, by the Japanese Patent Office as the International Searching Authority for International Application No. PCT/JP2022/022612.

Office Action (Notice of Reasons for Refusal) dated Jul. 21, 2026, in corresponding Japanese Patent Application No. 2025-150542 and machine English translation of the Office Action. (8 pages).

HYDROCARBON PRODUCTION APPARATUS AND HYDROCARBON PRODUCTION METHOD

CROSS-REFERENCE TO RELATED APPLICATIONS

This application is based upon and claims the benefit of priority from the prior Japanese Patent Application No. 2021-100351, filed on Jun. 16, 2021, and the International Patent Application No. PCT/JP2022/022612, filed on Jun. 3, 2022, the entire content of each of which is incorporated herein by reference.

BACKGROUND

Field of the Invention

The present invention relates to a hydrocarbon production apparatus and a hydrocarbon production method.

Description of the Related Art

A liquid fuel production technique using GTL (Gas to Liquid) is known (see Patent Literature 1). This production technique includes, as an example, a step of obtaining a synthesis gas containing hydrogen and carbon monoxide from natural gas, and a step of producing a liquid hydrocarbon having a high energy density by Fischer-Tropsch reaction (hereinafter, appropriately referred to as "FT reaction") using, as a raw material, the synthesis gas containing hydrogen and carbon monoxide.

Patent Literature 1: JP 2008-248179 A

In recent years, reduction of carbon dioxide generated in various economic activities has become one of major problems. When carbon dioxide contained in exhaust gas or the like is used for the production of hydrocarbon described above, it can greatly contribute to the realization of carbon-neutral. The present inventors have conducted intensive studies on a hydrocarbon production technique from such a viewpoint, and as a result, have arrived at a technique for improving the production efficiency of hydrocarbons.

SUMMARY OF THE INVENTION

The present invention has been made in view of such a situation, and an object thereof is to provide a technique for improving the production efficiency of hydrocarbons.

One aspect of the present invention is a hydrocarbon production apparatus. This apparatus includes a reverse shift reaction unit structured to reduce carbon dioxide to carbon monoxide by a reverse shift reaction by using carbon dioxide and hydrogen as source gases to obtain a synthesis gas containing carbon monoxide and hydrogen, a hydrocarbon production unit structured to produce a hydrocarbon by using the synthesis gas, a gas-liquid separation unit structured to separate a gas component containing hydrogen, carbon dioxide, and a light hydrocarbon having 4 or less carbon atoms and a liquid component containing a hydrocarbon having 5 or more carbon atoms from an effluent from the hydrocarbon production unit, a first separation unit structured to separate hydrogen and carbon dioxide, and a light hydrocarbon from the gas component, and a catalytic reaction unit structured to receive supply of the light hydrocarbon separated by the first separation unit to generate hydrogen and carbon monoxide by using the light hydrocarbon. The reverse shift reaction unit receives supply of the hydrogen and carbon dioxide separated by the first separation unit and also uses the hydrogen and carbon dioxide for generation of the synthesis gas. The hydrocarbon production unit receives supply of the hydrogen and carbon monoxide generated by the catalytic reaction unit and also uses the hydrogen and carbon monoxide for production of the hydrocarbon.

Another aspect of the present invention is a hydrocarbon production method. This method includes a reverse shift reaction step of reducing carbon dioxide to carbon monoxide by a reverse shift reaction by using carbon dioxide and hydrogen as source gases to obtain a synthesis gas containing carbon monoxide and hydrogen, a hydrocarbon production step of producing a hydrocarbon by using the synthesis gas, a gas-liquid separation step of separating a gas component containing hydrogen, carbon dioxide, and a light hydrocarbon having 4 or less carbon atoms and a liquid component containing a hydrocarbon having 5 or more carbon atoms from an effluent from the hydrocarbon production step, a first separation step of separating hydrogen and carbon dioxide, and a light hydrocarbon from the gas component, and a catalytic reaction step of receiving supply of the light hydrocarbon separated by the first separation step to generate hydrogen and carbon monoxide by using the light hydrocarbon. In the reverse shift reaction step, supply of the hydrogen and carbon dioxide separated by the first separation step is received and the hydrogen and carbon dioxide are also used for generation of the synthesis gas. In the hydrocarbon production step, supply of the hydrogen and carbon monoxide generated by the catalytic reaction step is received and the hydrogen and carbon monoxide are also used for production of the hydrocarbon.

Any combination of the aforementioned components or any manifestation of the present disclosure realized by modifications of a method, apparatus, system, and so forth, is effective as an embodiment of the present disclosure.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1:
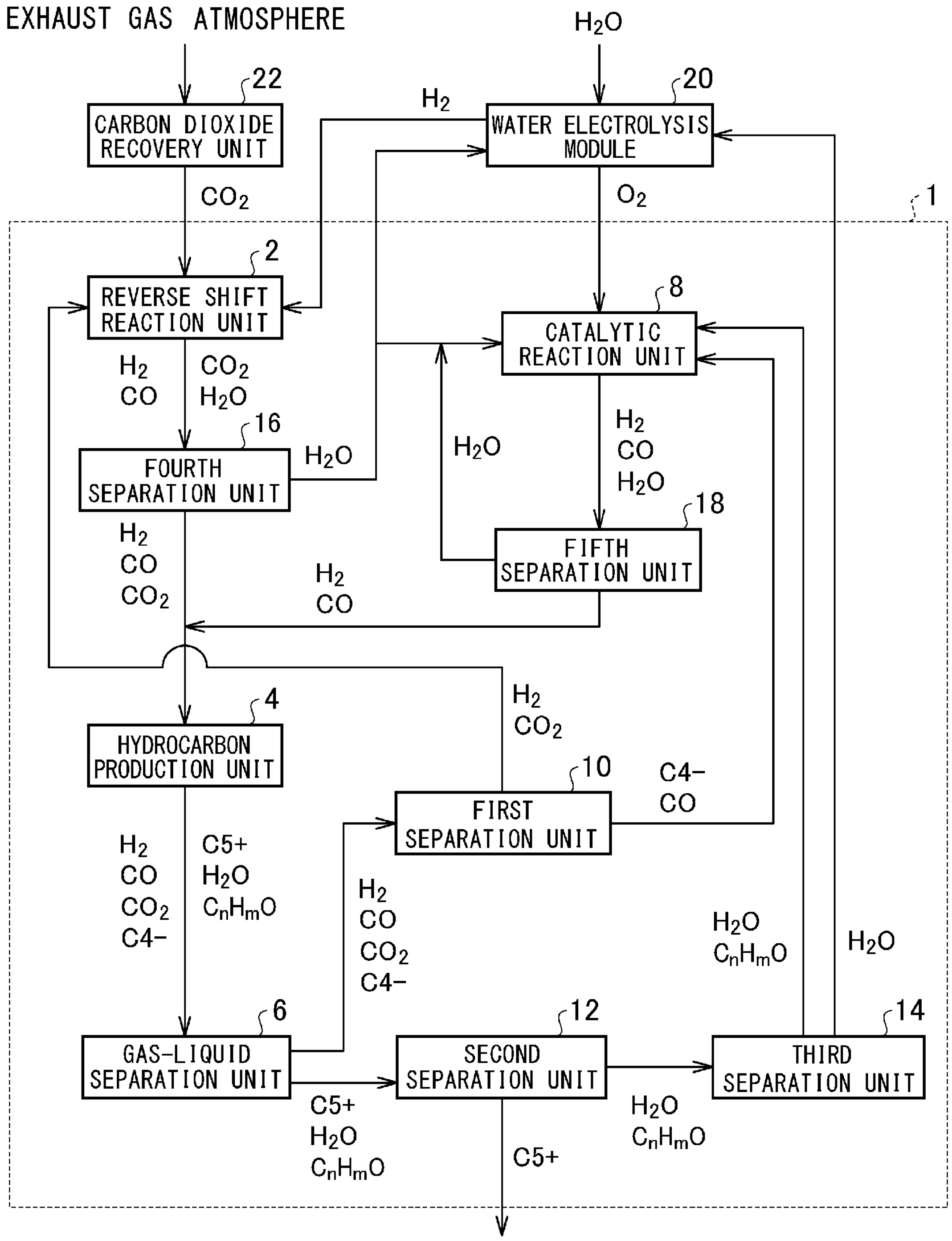
FIG. 1 is a schematic diagram of a hydrocarbon production apparatus according to an embodiment.

Hereinafter, the present invention will be described based on preferred embodiments with reference to the drawings. The embodiments are not intended to limit the technical scope of the present invention but are examples, and all features described in the embodiments and combinations thereof are not necessarily essential to the invention. Therefore, the contents of the embodiments can be subjected to many design changes such as changes, additions, and deletions of components without departing from the spirit of the invention defined in the claims. A new embodiment to which the design change is made has an effect of each of the combined embodiment and modifications.

In the embodiment, the contents that can be changed in design are emphasized with notations such as "of the present embodiment" and "in the present embodiment", but the design change is allowed even in the contents without such notations. Any combination of the components described in the embodiment is also effective as an aspect of the present invention. The same or equivalent components, members, and processing illustrated in the drawings are denoted by the same reference signs, and the redundant description will be omitted as appropriate. Scales and shapes of parts illustrated in the drawings are set for the sake of convenience in order to facilitate the description, and are not limitedly interpreted unless otherwise specified. When the terms "first", "second", and the like are used in the present specification or claims, these terms do not represent any order or importance, and are intended to distinguish one configuration from another configuration. In the drawings, some of the members that are not important for describing the embodiments are omitted.

FIG. 1 is a schematic diagram of a hydrocarbon production apparatus 1 according to an embodiment. The hydrocarbon production apparatus 1 includes a reverse shift reaction unit 2, a hydrocarbon production unit 4, a gas-liquid separation unit 6, a catalytic reaction unit 8, a first separation unit 10, a second separation unit 12, a third separation unit 14, a fourth separation unit 16, and a fifth separation unit 18.

The reverse shift reaction unit 2 is disposed upstream of the hydrocarbon production unit 4. The fourth separation unit 16 is disposed between the reverse shift reaction unit 2 and the hydrocarbon production unit 4. The gas-liquid separation unit 6 is disposed downstream of the hydrocarbon production unit 4. The first separation unit 10 is disposed between the gas-liquid separation unit 6 and the reverse shift reaction unit 2, and between the gas-liquid separation unit 6 and the catalytic reaction unit 8. The second separation unit 12 is disposed in parallel with the first separation unit 10 between the gas-liquid separation unit 6 and the catalytic reaction unit 8. The third separation unit 14 is disposed between the second separation unit 12 and the catalytic reaction unit 8. The fifth separation unit 18 is disposed between the catalytic reaction unit 8 and the hydrocarbon production unit 4.

The reverse shift reaction unit 2 receives supply of carbon dioxide and hydrogen as source gases. Carbon dioxide is reduced to carbon monoxide by a reverse shift reaction by using carbon dioxide and hydrogen to obtain a synthesis gas containing carbon monoxide and unreacted hydrogen.

As an example, the reverse shift reaction unit 2 of the present embodiment receives supply of hydrogen from a water electrolysis module 20. In FIG. 1, the water electrolysis module 20 is illustrated as an external device with respect to the hydrocarbon production apparatus 1, but the water electrolysis module 20 may be incorporated in the hydrocarbon production apparatus 1.

The water electrolysis module 20 is an electrolyzer that generates hydrogen and oxygen by electrolysis of water. As an example, the water electrolysis module 20 has a structure in which an oxygen generating electrode having a catalyst such as iridium or platinum and a hydrogen generating electrode having a catalyst such as platinum are separated from each other by a membrane having proton conductivity. That is, the water electrolysis module 20 is a solid polymer water electrolysis module. Other examples of the water electrolysis module 20 include alkaline water electrolysis module and a solid oxide water electrolysis module. The reactions during water electrolysis in the solid polymer water electrolysis module are as shown in the following Formulas (1) and (2).

Reaction taking place at the oxygen generating electrode: $2H_2O \rightarrow O_2+4H++4e^-$ (1)

Reaction taking place at the hydrogen generating electrode: $4H++4e^- \rightarrow 2H_2$ (2)

The water electrolysis module 20 receives supply of electric power necessary for water electrolysis from a power supply device (not illustrated). Examples of the power supply device include a power generation device that generates power using renewable energy, such as a wind power generation device or a solar power generation device. This makes it possible to reduce the emission amount of carbon dioxide associated with the generation of hydrogen and the production of a hydrocarbon having 5 or more carbon atoms (hereinafter, appropriately referred to as "C5+ component") as a target substance. The power supply device is not limited to a power generation device using renewable energy, and may be a system power supply, a power storage device storing electric power from the renewable energy power generation device and/or the system power supply, or the like. A combination of two or more of these devices may be used. However, in order to contribute to the realization of carbon-neutral, the power supply device is preferably a power generation device using renewable energy. When a system power supply, power storage device, or the like is used as the power supply device, it is preferable that the emission amount of carbon dioxide associated with these power generation and power storage is equal to or less than the emission amount of carbon dioxide in the power generation device using renewable energy.

As an example, the reverse shift reaction unit 2 of the present embodiment receives supply of carbon dioxide from a carbon dioxide recovery unit 22. In FIG. 1, the carbon dioxide recovery unit 22 is illustrated as an external device with respect to the hydrocarbon production apparatus 1, but the carbon dioxide recovery unit 22 may be incorporated in the hydrocarbon production apparatus 1. It is not meant that the entire hydrocarbon production apparatus 1 is one reactor.

The carbon dioxide recovery unit 22 can recover, for example, carbon dioxide from the atmosphere by direct air capture (DAC) or the like. The carbon dioxide recovery unit 22 can separate and recover carbon dioxide from exhaust gas discharged from thermal power generation, a chemical plant, or the like by a chemical adsorption method or the like. When the reverse shift reaction unit 2 receives supply of carbon dioxide from the carbon dioxide recovery unit 22, reduction of carbon dioxide in the atmosphere or the exhaust gas can be expected. The consumption of fossil fuel associated with the production of the C5+ component can be reduced.

In the reverse shift reaction unit 2, a reverse shift reaction shown in the following Formula (3) occurs to reduce carbon dioxide to carbon monoxide. As a result, a synthesis gas containing at least carbon monoxide and unreacted hydrogen is obtained. Water generated by the reverse shift reaction is also contained in the synthesis gas. Unreacted carbon dioxide may also be contained in the synthesis gas.

$$H_2+CO_2 \rightarrow CO+H_2O \quad (3)$$

The reaction temperature in the reverse shift reaction unit 2 is, for example, 290° C. or higher and 1100° C. or lower, preferably 700° C. or higher and 1100° C. or lower, and more preferably 700° C. or higher and 950° C. or lower. The reverse reaction of Formula (3) is called a water-gas-shift reaction. As a catalyst for the reverse shift reaction, a catalyst for a water-gas-shift reaction may be used. However, the reaction temperature of 700° C. or higher is much higher than the temperature in a general water-gas-shift reaction. Therefore, when the reaction temperature is set to a high temperature of 700° C. or higher, a general water-gas-shift catalyst is not suitable for use.

On the other hand, the reverse shift reaction unit 2 of the present embodiment contains a composite oxide having a perovskite structure $ABO_3$ as a reverse shift catalyst. In the perovskite structure $ABO_3$, A is an alkaline earth metal selected from the group consisting of calcium (Ca), strontium (Sr), and barium (Ba), and is preferably barium. B is a metal selected from the group consisting of titanium (Ti), aluminum (Al), zirconium (Zr), iron (Fe), tungsten (W), and molybdenum (Mo), and is preferably zirconium. When B is titanium or zirconium, a part thereof may be substituted with manganese (Mn), iron (Fe), or cobalt (Co), and preferably a part thereof is substituted with manganese. It is preferable that the reverse shift catalyst does not have an acid point that cleaves a bond between carbon atoms of a hydrocarbon and does not have a hydrogen dissociation ability that cleaves a bond between hydrogen atoms of hydrogen. The reverse shift catalyst having such characteristics can be screened, for example, by checking that a hydrocarbon having 8 carbon atoms by a dimerization reaction and isobutane by a hydrogenation reaction are not generated in a catalytic reaction using a mixed gas composed of isobutene and hydrogen. By using such a reverse shift catalyst, it is possible to realize the reverse shift reaction while suppressing side reactions such as methanation at a high temperature of 700° C. or higher.

It is preferable to use an atomic absorption spectrophotometer, a Fourier transform infrared spectrophotometer, or the like to measure whether or not the source gas of the reverse shift reaction contains a metal component. It is preferable to install a filter capable of removing fine powder of a carbonized metal generated by carburization and an adsorbent capable of removing a metal carbonyl on a recycle line through which carbon monoxide flows. The filter is preferably made of ceramic, and the adsorbent is preferably Y-type zeolite.

When the synthesis gas obtained by the reverse shift reaction is used for production of the hydrocarbon, a carbon dioxide removal device may be installed between the reverse shift reaction unit 2 and the hydrocarbon production unit 4 in order to reduce the concentration of carbon dioxide in the synthesis gas. By adopting the above-described reverse shift catalyst and performing the reverse shift reaction at a high temperature, a $CO/(CO+CO_2)$ ratio at the outlet of the reverse shift reaction unit 2 can be improved. The $CO/(CO+CO_2)$ ratio is a value calculated from the carbon monoxide concentration and the carbon dioxide concentration at the outlet of the reverse shift reaction unit 2. That is, the $CO/(CO+CO_2)$ ratio is a ratio at which carbon dioxide of the raw material is converted (reduced) to carbon monoxide. Therefore, the carbon dioxide concentration at the outlet of the reverse shift reaction unit 2 can be reduced. Thereby, the partial pressure of the synthesis gas composed of carbon monoxide and hydrogen in the hydrocarbon production unit 4 can be increased to improve the carbon monoxide conversion rate and the selectivity of the C5+ component. The heat energy required for the carbon dioxide removal device can be supplied from the hydrocarbon production unit 4 using the FT reaction which is an exothermic reaction. This makes it possible to reduce the energy required for the production of a hydrocarbon and to improve the production efficiency of the C5+ component as a target substance.

By performing the reverse shift reaction at a high temperature of 700° C. or higher, generation of oxygenated hydrocarbon or the like can be suppressed. This makes it possible to suppress the oxygenated hydrocarbon as an impurity from being contained in by-product water. Therefore, the water separated by the fourth separation unit 16 located downstream of the reverse shift reaction unit 2 can be recycled to the water electrolysis module 20 without being subjected to a purification treatment (removal of oxygenated impurities). When the high-temperature reverse shift reaction is not performed, a water purification treatment can be performed by supplying the water separated by the fourth separation unit 16 to the third separation unit 14 described below.

By adopting the above-described reverse shift catalyst, it is possible to easily suppress the methanation reaction in which methane is generated from carbon dioxide as compared with a conventional Ni catalyst or the like. This also makes it possible to improve the $CO/(CO+CO_2)$ ratio. By improving the $CO/(CO+CO_2)$ ratio, the yield of the liquid component in the hydrocarbon production unit 4 can be increased.

In the present embodiment, as described below, the off-gas of the hydrocarbon production unit 4 is recycled to improve the production efficiency of the C5+ component, but energy is also required for this recycling. The amount of recycled off-gas can be suppressed by increasing the yield of the liquid component by improvement of the $CO/(CO+CO_2)$ ratio. Therefore, it is possible to reduce the auxiliary power required for recycling, the energy required for separating the off-gas, the heat amount required for the catalytic reaction at the recycling destination, and the like. As a result, improvement in production efficiency can be expected as the entire process of producing the C5+ component.

The synthesis gas flowing out of the reverse shift reaction unit 2 is sent to the fourth separation unit 16. The fourth separation unit 16 can be constituted by a known gas-liquid separation unit, and separates water from the synthesis gas. The water separated by the fourth separation unit 16 is supplied to the water electrolysis module 20 and used for generation of hydrogen. The water separated by the fourth separation unit 16 is supplied to the catalytic reaction unit 8 and used for the catalytic reaction in the catalytic reaction unit 8. This makes it possible to improve the production efficiency of the C5+ component. The recycling of the water separated from the synthesis gas may be performed on only one of the water electrolysis module 20 and the catalytic reaction unit 8, or may not be performed on both of them.

The synthesis gas from which water is separated by the fourth separation unit 16 is sent to the hydrocarbon production unit 4. The hydrocarbon production unit 4 produces a C5+ component as a target substance by using the supplied synthesis gas. The C5+ component is, for example, normal paraffin. The hydrocarbon production unit 4 of the present embodiment is constituted by a known FT reactor. As the FT reactor, a tubular fixed bed reactor, a slurry bed reactor, or the like can be used. In the hydrocarbon production unit 4, the FT reaction shown in Formula (4) described below occurs, and a C5+ component is generated by carbon-carbon chain growth. As a catalyst for FT reaction, a cobalt catalyst, a precipitated iron catalyst, a ruthenium catalyst, or the like can be used.

The proportion of a reaction intermediate having n carbon atoms to be heavy into a reaction intermediate having n+1 carbon atoms by carbon-carbon chain growth is represented by a chain growth probability α. α varies depending on the type of catalyst and reaction conditions, and is preferably 0.75 to 0.95 and more preferably 0.85 to 0.95. In Formula (4), for example, when α is 0.95, n of the C5+ component contained in an amount of 0.1 mol % or more is an integer of 5 to 60. In the hydrocarbon production unit 4, a gaseous light hydrocarbon having 4 or less carbon atoms at normal temperature and normal pressure (hereinafter, appropriately referred to as "C4− component") such as methane, ethane, propane, and butane are also produced as by-products.

$$nCO+(2n+1)H_2 \rightarrow C_nH_{2n+2}+nH_2O \tag{4}$$

An effluent from the hydrocarbon production unit 4 is sent to the gas-liquid separation unit 6. The effluent may contain not only a C5+ component and a C4− component, but also water and oxygenated hydrocarbon (such as $C_nH_mO$) as other by-products, unreacted hydrogen, carbon monoxide, carbon dioxide, and the like. The oxygenated hydrocarbon is a hydrocarbon compound containing oxygen, and is hydrophilic and easily dissolved in water. Examples of the oxygenated hydrocarbon include alcohols, carboxylic acids, esters, ethers, and ketones. The gas-liquid separation unit 6 can be constituted by a known gas-liquid separation unit, and separates a liquid component and a gas component from the effluent. The gas-liquid separation is preferably performed in two stages of high temperature and low temperature. This makes it possible to prevent the gas-liquid separation unit 6 from being blocked by a heavy hydrocarbon. For example, high-temperature gas-liquid separation can be performed at 80° C., and low-temperature gas-liquid separation can be performed at 40° C. When the gas-liquid separation unit is in a high pressure state, the temperature at the time of gas-liquid separation may be increased to a temperature lower than the boiling point temperature of water at the partial pressure of water by 20° C. The liquid component contains an oily component containing a C5+ component and an aqueous component containing water and an oxygenated hydrocarbon. The gas component contains hydrogen, carbon monoxide, carbon dioxide, and a C4− component.

Gas Separation Recycling Treatment

The gas component separated by the gas-liquid separation unit 6 is sent to the first separation unit 10. The first separation unit 10 separates hydrogen and carbon dioxide, and a C4− component from the gas component (first separation step). Carbon monoxide is included on the side of the C4− component. Carbon monoxide may be included on the side of the hydrogen and the carbon dioxide. As an example, the first separation unit 10 performs separation by using at least one of a pressure swing adsorption (PSA) method and a membrane separation method. When the first separation unit uses a membrane separation method, as an example, the first separation unit 10 includes at least one of a polyimide film, a carbon film obtained by carbonizing the polyimide film, and a metal film containing Pd.

The hydrogen and carbon dioxide separated by the first separation unit 10 are sent to the reverse shift reaction unit 2. The reverse shift reaction unit 2 receives supply of the hydrogen and carbon dioxide separated by the first separation unit 10 and also uses the hydrogen and carbon dioxide for generation of the synthesis gas. This makes it possible to increase the utilization rate of the hydrogen and carbon dioxide supplied as raw materials and to improve the production efficiency of the C5+ component. When the recycled gas supplied to the reverse shift reaction unit 2 contains a large amount of compounds other than hydrogen and carbon dioxide, which are reactants in the reverse shift reaction unit 2, a reverse reaction may occur aiming at an equilibrium composition in the reverse shift reaction unit 2. As a result, the amount of carbon monoxide produced can be reduced. On the other hand, by sending the hydrogen and carbon dioxide separated by the first separation unit 10 to the reverse shift reaction unit 2, the reverse reaction can be suppressed. Therefore, the production efficiency of the C5+ component can be further improved.

The C4− component and carbon monoxide separated by the first separation unit 10 are sent to the catalytic reaction unit 8. The catalytic reaction unit 8 receives supply of the C4− component separated by the first separation unit 10 and generates hydrogen and carbon monoxide by using the C4− component. When the C4− component is sent to the reverse shift reaction unit 2 without providing the first separation unit 10, the C4− component is hardly reacted in the reverse shift reaction unit 2, and thus is accumulated in the system. As a result, the partial pressure of the synthesis gas in the system decreases, and the reaction in the hydrocarbon production unit 4 may be inhibited. On the other hand, in the present embodiment, the C4− component separated by the first separation unit 10 is sent to the catalytic reaction unit 8 and used for generation of hydrogen and carbon monoxide. This makes it possible to further improve the production efficiency of the C5+ component. Carbon monoxide is also used for the reaction in the catalytic reaction unit 8.

Carbon dioxide is not involved in the reaction in the catalytic reaction unit 8. Carbon dioxide is generally a non-flammable substance. Therefore, even when the catalytic reaction unit 8 performs a partial oxidation reaction or an autothermal reforming reaction described below, carbon dioxide is not used for combustion. Therefore, when carbon dioxide is sent to the catalytic reaction unit 8 without providing the first separation unit 10, the carbon dioxide is also heated at the time of increasing the temperature of the catalytic reaction unit 8 to the reaction temperature of the catalytic reaction, so that the required energy may be increased. On the other hand, in the present embodiment, the carbon dioxide separated by the first separation unit 10 is sent to the reverse shift reaction unit 2 and used for generation of the synthesis gas. This makes it possible to suppress an increase in required energy in the catalytic reaction unit 8 and to further improve the production efficiency of the C5+ component.

For example, the catalytic reaction unit 8 generates hydrogen and carbon monoxide from the C4− component by any of a steam reforming reaction, a partial oxidation reaction, and an autothermal reforming reaction. Preferably, the catalytic reaction unit 8 generates hydrogen and carbon monoxide from the C4− component by a reforming reaction (at least one of a steam reforming reaction and an autothermal reforming reaction). When oxygen is required for the reaction taking place in the catalytic reaction unit 8, this oxygen is supplied, for example, from the water electrolysis module 20.

When the catalytic reaction unit 8 generates hydrogen and carbon monoxide from the C4− component by a steam reforming reaction, the catalytic reaction unit 8 can be constituted by a known steam reformer. In this case, as an example, the catalytic reaction unit 8 generates methane from the C4− component by a preceding stage reaction in which a steam reforming reaction is performed at a first temperature, and generates carbon monoxide and hydrogen from the methane by a subsequent stage reaction in which a steam reforming reaction is performed at a second temperature higher than the first temperature. The catalytic reaction unit 8 may include a reactor for the preceding stage reaction and a reactor for the subsequent stage reaction, and may change a temperature in one reactor from the first temperature to the second temperature. The first temperature is, for example, 450 to 600° C. and preferably 450 to 500° C. The second temperature is, for example, 750° C. or higher. A difference in reaction temperature between the preceding stage and the subsequent stage is preferably 150° C. or higher and more preferably 250° C. or higher.

When a C4− component having 2 or more carbon atoms is directly subjected to the reforming reaction at the second temperature, adjacent carbon atoms are each converted into carbon monoxide, a disproportionation reaction occurs between adjacent carbon monoxides, and coke (carbon) deposition is likely to occur. In the C4− component having 2 or more carbon atoms, there is a high possibility that olefin production by a dehydrogenation reaction and coke (heavy hydrocarbon) deposition by polymerization thereof occur at 850° C. or lower. When the coke is deposited, catalyst deterioration or clogging of a reaction device may occur. By converting the C4− component into mainly methane in the preceding stage reaction and then subjecting the methane to the subsequent stage reaction, it is possible to generate hydrogen and carbon monoxide while suppressing catalyst deterioration and the like due to coke deposition. This makes it possible to extend the use period of the catalytic reaction unit 8 and to improve the production efficiency of the C5+ component.

As a method for suppressing coke deposition, it is conceivable to increase an O/C ratio (oxygen/carbon ratio) by supplying water in an amount of competing for an active point between adjacent carbon monoxides. That is, when a plurality of COs are localized, coke is likely to be deposited due to disproportionation of CO. Therefore, by supplying water to cause a shift reaction between water and CO, coke deposition is suppressed. The O/C ratio is a ratio of the number of moles (0) of oxygen atoms to be supplied into the catalytic reaction unit 8 to the number of moles (C) of carbon atoms to be supplied into the catalytic reaction unit 8. When all the oxygen atoms in the raw material are derived from water, the number of moles of oxygen atoms is equal to the number of moles of steam, that is, the O/C ratio is equal to the S/C ratio (steam/carbon ratio). However, in the case of supplying water, the heat amount required for heating the water increases, and thus the energy efficiency required for the production of the C5+ component decreases. On the other hand, by using the above-described two-stage reforming reaction, it is possible to suppress an increase in the supply amount of water for the purpose of suppressing coke deposition. Therefore, the energy required for the production of the C5+ component can be reduced, and the production efficiency of the C5+ component can be improved.

When the steam reforming is performed in two stages of the first temperature and the second temperature, it is considered that an equilibrium reaction shown in the following Formulas (5) to (8) occurs in the catalytic reaction unit 8. Therefore, the first temperature is set so that a pre-reforming reaction shown in the following Formulas (5) to (7) occurs as the preceding stage reaction to mainly generate methane. At this time, the S/C ratio is preferably 2.5 to 3.0. The reaction shown in Formula (7) is an exothermic reaction. Therefore, with the same composition and pressure, the lower the temperature, the higher the yield of methane. Subsequently, the second temperature is set so that a reaction shown in the following Formula (8) occurs as the subsequent stage reaction to produce a synthesis gas containing carbon monoxide and hydrogen. The reaction shown in Formula (8) is a reverse reaction of Formula (7) and is an endothermic reaction. Therefore, with the same composition and pressure, the higher the temperature, the higher the yield of carbon monoxide and hydrogen. For example, the S/C ratio at the second temperature is 1.0 to 2.5. It is preferable that the S/C ratio can be adjusted by not adding water consumed in the preceding stage reaction. In Formula (5), the C4− component is expressed as $C_nH_m$, n is an integer of 1 to 4, and m is an integer of 4 to 10. In the following reaction formulas, the C4− component is expressed in the same manner.

$$C_nH_m+nH_2O \rightarrow nCO+(n+m/2)H_2 \quad (5)$$

$$CO+H_2O \rightarrow CO_2+H_2 \quad (6)$$

$$CO+3H_2 \rightarrow CH_4+H_2O \quad (7)$$

$$CH_4+H_2O \rightarrow CO+3H_2 \quad (8)$$

When the catalytic reaction unit 8 generates hydrogen and carbon monoxide from the C4− component by an autothermal reforming reaction, the catalytic reaction unit 8 can be constituted by a known autothermal reformer. In this case, in the catalytic reaction unit 8, first, a reaction shown in the following Formula (9) occurs, and subsequently, a reaction shown in the following Formula (10) occurs. The reaction shown in Formula (9) is an exothermic reaction. On the other hand, the reaction shown in Formula (10) is an endothermic reaction. Heat necessary for the reaction shown in Formula (10) is covered by heat generated by the reaction shown in Formula (9). In the reaction shown in Formula (9), the by-product oxygen generated by the water electrolysis module 20 can be used.

$$C_nH_m+(n/2)O_2 \rightarrow nCO+(m/2)H_2 \quad (9)$$

$$C_nH_m+nH_2O \rightarrow nCO+(n+m/2)H_2 \quad (10)$$

When the catalytic reaction unit 8 generates hydrogen and carbon monoxide from the C4− component by a partial oxidation reaction, the catalytic reaction unit 8 can be constituted by a known partial oxidation reactor. In this case, in the catalytic reaction unit 8, a reaction shown in the following Formula (11) occurs. In the reaction shown in Formula (11), the by-product oxygen generated by the water electrolysis module 20 can be used.

$$C_nH_m+(n/2)O_2 \rightarrow nCO+(m/2)H_2 \quad (11)$$

When the catalytic reaction unit 8 is constituted by an autothermal reformer, a preliminary reformer (not illustrated) for performing the above-described pre-reforming reaction may be provided between the first separation unit 10 and the catalytic reaction unit 8. This pre-reforming reaction is performed at the above-described first temperature. As a result, the reactions shown in the above Formulas (5) to (7) occur, the C4− component sent from the first separation unit 10 is reformed into methane by the preliminary reformer, and the methane can be subjected to the autothermal reforming reaction. As a result, it is possible to generate hydrogen and carbon monoxide while suppressing catalyst deterioration due to coke deposition and suppressing an increase in the S/C ratio as described above. Therefore, the production efficiency of the C5+ component can be further improved.

The effluent from the catalytic reaction unit 8 is sent to the fifth separation unit 18. This effluent may contain unreacted water as well as hydrogen and carbon monoxide. The fifth separation unit 18 can be constituted by a known gas-liquid separation unit, and separates hydrogen and carbon monoxide, and water from the effluent. The water separated by the fifth separation unit 18 is sent to the catalytic reaction unit 8 and reused for the reaction in the catalytic reaction unit 8. When the catalytic reaction unit 8 performs only the partial oxidation reaction, the supply of the water from the fifth separation unit 18 to the catalytic reaction unit 8 is omitted. Similarly, when the catalytic reaction unit 8 performs only the partial oxidation reaction, the supply of the water from the fourth separation unit 16 described above and the supply of the aqueous component from the third separation unit 14 described below are also omitted.

From the viewpoint of simplification of the structure of the hydrocarbon production apparatus 1, it is conceivable that the fifth separation unit 18 is omitted and the effluent from the catalytic reaction unit 8 is sent to the fourth separation unit 16. However, the effluent from the catalytic reaction unit 8 may contain an oxygenated hydrocarbon. Therefore, it is desirable that the fifth separation unit 18 is provided separately from the fourth separation unit 16, and water is looped between the catalytic reaction unit 8 and the fifth separation unit 18.

The hydrogen and carbon monoxide separated by the fifth separation unit 18 are sent to the hydrocarbon production unit 4. The hydrocarbon production unit 4 receives supply of the hydrogen and carbon monoxide generated by the catalytic reaction unit 8 and also uses the hydrogen and carbon monoxide for generation of the C5+ component. This makes it possible to improve the utilization rate of the hydrogen and carbon dioxide supplied as raw materials and to improve the production efficiency of the C5+ component.

Aqueous Component Recycling Treatment

The liquid component separated by the gas-liquid separation unit 6 is sent to the second separation unit 12. The second separation unit 12 can be constituted by a known oil-water separator, and separates an oily component and an aqueous component from the liquid component (second separation step). The C5+ component contained in the oily component separated by the second separation unit 12 is subjected to an upgrade treatment by catalytic reforming, hydrogenolysis, hydrogenation purification, alkylation, isomerization, or the like as necessary, and is used, for example, as a substitute for jet fuel, gasoline, kerosene, or the like. When the oily component derived from crude oil containing a hetero element such as sulfur or nitrogen is not treated by an upgrade apparatus and thus the gas component derived from crude oil is not contained in the effluent from the upgrade apparatus, the C4− component by-produced by the upgrade apparatus may be returned to the first separation unit 10. This makes it possible to enhance the production efficiency as a substitute for jet fuel or the like.

A part of the aqueous component separated by the second separation unit 12 is sent to the catalytic reaction unit 8. The catalytic reaction unit 8 receives supply of the aqueous component separated by the second separation unit 12, and the aqueous component is also used for generation of hydrogen and carbon monoxide. This makes it possible to convert water in the aqueous component into hydrogen in the catalytic reaction unit 8. Therefore, since the amount of hydrogen supplied as a raw material can be reduced, the production efficiency of the C5+ component can be improved. The oxygenated hydrocarbon in the aqueous component can be converted into carbon monoxide in the catalytic reaction unit 8. This also makes it possible to improve the production efficiency of the C5+ component. A part of the aqueous component separated by the second separation unit 12 is sent to the water electrolysis module 20. The water electrolysis module 20 receives supply of the aqueous component separated by the second separation unit 12 and generates hydrogen by using the aqueous component.

In the present embodiment, the aqueous component separated by the second separation unit 12 is sent to the catalytic reaction unit 8 and the water electrolysis module 20 through the third separation unit 14. The third separation unit 14 separates at least a part of water from the aqueous component. In the third separation unit 14, water substantially free of oxygenated hydrocarbon and water in which the oxygenated hydrocarbon is concentrated are obtained. That is, the water purification treatment is performed. As an example, the third separation unit 14 performs separation by using at least one of a pressure swing adsorption (PSA) method, a precision distillation method, and a membrane separation method. When the third separation unit 14 uses a membrane separation method, as an example, the third separation unit 14 includes at least one of a reverse osmosis membrane, a zeolite membrane, and a carbon membrane.

The water separated by the third separation unit 14, that is, water from which oxygenated hydrocarbon has been removed, in other words, purified water is supplied to the water electrolysis module 20. The water electrolysis module 20 receives supply of the water separated by the third separation unit 14 and generates hydrogen by using the water. By supplying the water from which oxygenated hydrocarbon has been removed to the water electrolysis module 20, catalyst deterioration in the water electrolysis module 20 can be suppressed. Therefore, the use period of the water electrolysis module 20 can be extended, and the production efficiency of the C5+ component can be improved.

The aqueous component from which water is separated by the third separation unit 14, in other words, the water in which the oxygenated hydrocarbon is concentrated is supplied to the catalytic reaction unit 8. The catalytic reaction unit 8 receives supply of the aqueous component from which water is separated by the third separation unit 14, and the aqueous component is used for generation of hydrogen and carbon monoxide. The catalytic reaction unit 8 generates hydrogen and carbon monoxide from the oxygenated hydrocarbon by the reforming reaction.

When the catalytic reaction unit 8 generates hydrogen and carbon monoxide from the oxygenated hydrocarbon by a steam reforming reaction, the catalytic reaction unit 8 can be constituted by a known steam reformer. In this case, as an example, the catalytic reaction unit 8 generates methane from the oxygenated hydrocarbon by a preceding stage reaction in which a steam reforming reaction is performed at a first temperature, and generates carbon monoxide and hydrogen from the methane by a subsequent stage reaction in which a steam reforming reaction is performed at a second temperature higher than the first temperature. The first temperature is, for example, 450 to 600° C. and preferably 450 to 500° C. The second temperature is, for example, 750° C. or higher. A difference in reaction temperature between the preceding stage and the subsequent stage is preferably 150° C. or higher and more preferably 250° C. or higher.

By converting the oxygenated hydrocarbon into mainly methane in the preceding stage reaction and then subjecting the methane to the subsequent stage reaction, it is possible to produce hydrogen and carbon monoxide while suppressing catalyst deterioration and the like due to coke deposition and suppressing an increase in the S/C ratio, as in the case of the C4− component. This makes it possible to improve the production efficiency of the C5+ component. When the oxygenated hydrocarbon is converted into carbon monoxide and hydrogen in the two-stage reaction, the reaction temperature at the preceding stage can be lower than the reaction temperature at the subsequent stage. The reaction temperature at the preceding stage can be further lowered as compared with the case of the C4− component. This makes it possible to reduce the energy required for the production of the C5+ component and to further improve the production efficiency of the C5+ component.

When the steam reforming is performed in two stages of the first temperature and the second temperature, it is considered that an equilibrium reaction shown in the following Formulas (12) to (15) occurs in the catalytic reaction unit 8. Therefore, the first temperature is set so that a pre-reforming reaction shown in the following Formulas (12) to (14) occurs as the preceding stage reaction to mainly generate methane. At this time, the S/C ratio is preferably 2.5 to 3.0. The reaction shown in Formula (14) is an exothermic reaction. Therefore, with the same composition and pressure, the lower the temperature, the higher the yield of methane. Subsequently, the second temperature is set so that a reaction shown in the following Formula (15) occurs as the subsequent stage reaction to produce a synthesis gas containing carbon monoxide and hydrogen. The reaction shown in Formula (15) is a reverse reaction of Formula (14) and is an endothermic reaction. Therefore, with the same composition and pressure, the higher the temperature, the higher the yield of carbon monoxide and hydrogen. For example, the S/C ratio at the second temperature is 1.0 to 2.5. It is preferable that the S/C ratio can be adjusted by not adding water consumed in the preceding stage reaction. In Formula (12), n is, for example, an integer of 1 to 7, and m is, for example, an integer of 4 to 16. In the following reaction formulas, the numerical values of n and m in the oxygenated hydrocarbon are the same.

$$C_nH_mO+(n-1)H_2O=nCO+(n-1+m/2)H_2 \quad (12)$$

$$CO+H_2O\rightarrow CO_2+H_2 \quad (13)$$

$$CO+3H_2\rightarrow CH_4+H_2O \quad (14)$$

$$CH_4+H_2O\rightarrow CO+3H_2 \quad (15)$$

When the catalytic reaction unit 8 generates hydrogen and carbon monoxide from the oxygenated hydrocarbon by an autothermal reforming reaction, the catalytic reaction unit 8 can be constituted by a known autothermal reformer. In this case, in the catalytic reaction unit 8, first, a reaction shown in the following Formula (16) occurs, and subsequently, a reaction shown in the following Formula (17) occurs. The reaction shown in Formula (16) is an exothermic reaction. On the other hand, the reaction shown in Formula (17) is an endothermic reaction. Heat necessary for the reaction shown in Formula (17) is covered by heat generated by the reaction shown in Formula (16). In the reaction shown in Formula (16), the by-product oxygen generated by the water electrolysis module 20 can be used.

$$C_nH_mO+\{(n-1)/2\}O_2\rightarrow nCO+(m/2)H_2 \quad (16)$$

$$C_nH_mO+(n-1)H_2O=nCO+(n-1+m/2)H_2 \quad (17)$$

When the catalytic reaction unit 8 is constituted by an autothermal reformer, a preliminary reformer (not illustrated) for performing the above-described pre-reforming reaction may be provided between the third separation unit 14 and the catalytic reaction unit 8. This pre-reforming reaction is performed at the above-described first temperature. As a result, the reactions shown in the above Formulas (12) to (14) occur, the oxygenated hydrocarbon sent from the third separation unit 14 is reformed into methane by the steam reformer, and the methane can be subjected to the autothermal reforming reaction. As a result, it is possible to generate hydrogen and carbon monoxide while suppressing catalyst deterioration due to coke deposition and suppressing an increase in the S/C ratio as described above. Therefore, the production efficiency of the C5+ component can be further improved.

In the catalytic reaction unit 8, a dehydration reaction shown in the following Formula (18) and a dehydration condensation reaction shown in the following Formula (19) occur as side reactions, and water can be generated from a hydrogen-containing hydrocarbon. In Formulas (18) and (19), the numerical range of a is similar to n, and the numerical range of b is similar to m.

$$C_nH_mO=C_nH_{m-2}+H_2O \quad (18)$$

$$C_nH_mO+C_aH_bO=C_nH_{m-1}OC_aH_{b-1}+H_2O \quad (19)$$

In the catalytic reaction unit 8, coke deposition tends to occur due to a disproportionation reaction of carbon monoxide. As described above, water is required to suppress coke deposition. In general, water required for suppressing coke deposition is secured by increasing the supply amount of water. When the supply amount of water is increased, the S/C ratio in the catalytic reaction unit 8 increases and becomes larger than the stoichiometric ratio.

On the other hand, in the present embodiment, the amount of water to be supplied to the catalytic reaction unit 8 is reduced by separating at least a part of water by the third separation unit 14. This makes it possible to reduce the S/C ratio in the catalytic reaction unit 8. By supplying the oxygenated hydrocarbon to the catalytic reaction unit 8 and generating by-product water from the oxygenated hydrocarbon in the catalytic reaction unit 8, the by-product water can be used for suppressing coke deposition. Therefore, while reducing the supply amount of water to the catalytic reaction unit 8 to reduce the S/C ratio, coke deposition can be suppressed to suppress catalyst deterioration in the catalytic reaction unit 8. As a result, the use period of the catalytic reaction unit 8 can be extended, and the production efficiency of the C5+ component can be improved.

The energy efficiency required for the production of the C5+ component can be expressed by the following Formula (20).

Energy efficiency=Calorific value of the obtained C5+ component/(Calorific value of consumed raw material hydrogen+Required heat amount on premise of heat recovery for production+Power required for production of consumed raw material hydrogen+Heat amount and power required for recovery of consumed raw material carbon dioxide) (20)

The "required heat amount on premise of heat recovery for production" in Formula (20) means a heat amount added from the outside of the system on the premise that heat of a temperature difference between the inlet gas and the outlet gas in each reactor is recovered and the recovered heat is reused for the reaction.

Specifically, for example, the raw material to be supplied to the reverse shift reaction unit 2 needs to be heated to the reaction temperature (for example, 800° C.) in the reverse shift reaction unit 2. Since the reverse shift reaction is an endothermic reaction, it is necessary to add heat. On the other hand, in order to subject the synthesis gas obtained in the reverse shift reaction unit 2 to a gas-liquid separation treatment in the fourth separation unit 16, it is necessary to cool the synthesis gas. Therefore, heat of the synthesis gas (outlet gas) discharged in the reverse shift reaction unit 2 is recovered by a heat exchanger, and the recovered heat is transferred to the raw material (inlet gas). This makes it possible to reduce the fuel of a heating furnace for heating the raw material and the power of a chiller for cooling the synthesis gas.

For example, when the carbon dioxide recovery unit 22 separates and recovers carbon dioxide by a chemical adsorption method or the like, heat is required to dissipate the adsorbed carbon dioxide. On the other hand, the FT reaction occurring in the hydrocarbon production unit 4 is an exothermic reaction. Therefore, the heat generated in the hydrocarbon production unit 4 can be recovered by a heat exchanger, and the recovered heat can be used for the dissipation of carbon dioxide in the carbon dioxide recovery unit 22.

As described above, the heat that is insufficient even if the heat is recovered as much as possible needs to be generated in a heating furnace. The heat generated in this heating furnace corresponds to the "required heat amount on premise of heat recovery for production". When the catalytic reaction unit 8 is constituted by an autothermal reformer, the required heat amount can be reduced as compared with a case where the catalytic reaction unit 8 is constituted by a steam reformer.

When the supply amount of water to the catalytic reaction unit 8 increases, that is, when the S/C ratio increases, the heat amount required for heating the water increases. For this reason, the "required heat amount on premise of heat recovery for production" in Formula (20) increases, and the energy efficiency required for the production of the C5+ component decreases. On the other hand, when oxygenated hydrocarbon is supplied to the catalytic reaction unit 8 instead of water to reduce the S/C ratio, a C5+ component is generated from carbon monoxide derived from the oxygenated hydrocarbon, so that the "calorific value of the obtained C5+ component" in Formula (20) can be increased. As a result, the energy efficiency required for the production of the C5+ component is improved. Therefore, by reducing the supply amount of water to the catalytic reaction unit 8 and supplying oxygenated hydrocarbon instead, the production efficiency of the C5+ component can be further improved.

In a case where the catalytic reaction unit 8 is constituted by an autothermal reformer, when hydrogen and carbon dioxide are also supplied to the catalytic reaction unit 8 without providing the first separation unit 10, heat is required for heating the carbon dioxide, and it is difficult to cover the reaction heat required for the reforming reaction by partial oxidation of the C4− component. The insufficient reaction heat is covered by the combustion of hydrogen sent to the catalytic reaction unit 8 together with carbon dioxide.

When hydrogen burns, water is produced as a by-product. This water is used for the reforming reaction in the catalytic reaction unit 8. Therefore, the consumption of recycled water from the effluent of the hydrocarbon production unit 4 to the catalytic reaction unit 8 is delayed. When the recycled water is not consumed, the amount of by-product water required for a wastewater treatment increases. In other words, when by-product water is not recycled and converted into hydrogen used in the hydrocarbon production unit 4, the amount of hydrogen to be added from the outside of the hydrocarbon production apparatus 1 as a raw material increases. As a result, a $H_2/CO_2$ ratio (molar ratio) of the raw material to be supplied from the outside of the hydrocarbon production apparatus 1 (so-called fresh feed) increases.

On the other hand, when the catalytic reaction unit 8 is constituted by a steam reformer, combustion of hydrogen does not occur in the catalytic reaction unit 8, and by-product water is not generated. Therefore, even when hydrogen is supplied to the catalytic reaction unit 8, the water recycled from the hydrocarbon production unit 4 is used for the reforming reaction in the catalytic reaction unit 8. Therefore, it is possible to reduce the $H_2/CO_2$ ratio of the fresh feed as compared with a case where the catalytic reaction unit 8 is constituted by an autothermal reformer. When the $H_2/CO_2$ ratio of the fresh feed can be reduced, the power required for the production of hydrogen can be reduced. Therefore, a decrease in energy efficiency shown in Formula (20) can be suppressed.

Therefore, when the catalytic reaction unit 8 is constituted by a steam reformer, the effect of improving the production efficiency of the C5+ component by recycling the aqueous component can be more strongly exhibited. When the catalytic reaction unit 8 is constituted by an autothermal reformer, by combining the first separation unit 10, the improving effect can be more easily exhibited.

In the hydrocarbon production apparatus 1 according to one example, the molar ratio ($CO/H_2$ ratio) of carbon monoxide and hydrogen to be supplied to the hydrocarbon production unit 4 is preferably 1.5 or more and 4.0 or less, more preferably 2.0 or more and 3.5 or less, and still more preferably 2.2 or more and 3.0 or less. In order to suppress coke deposition in the catalytic reaction unit 8 and satisfy the $CO/H_2$ ratio described above, the S/C ratio in the preceding stage reaction is preferably 3.0 or more and 6.0 or less. The S/C ratio in the subsequent stage reaction is preferably 0.5 or more and 3.0 or less and more preferably 1.0 or more and 2.5 or less.

Figure 2:
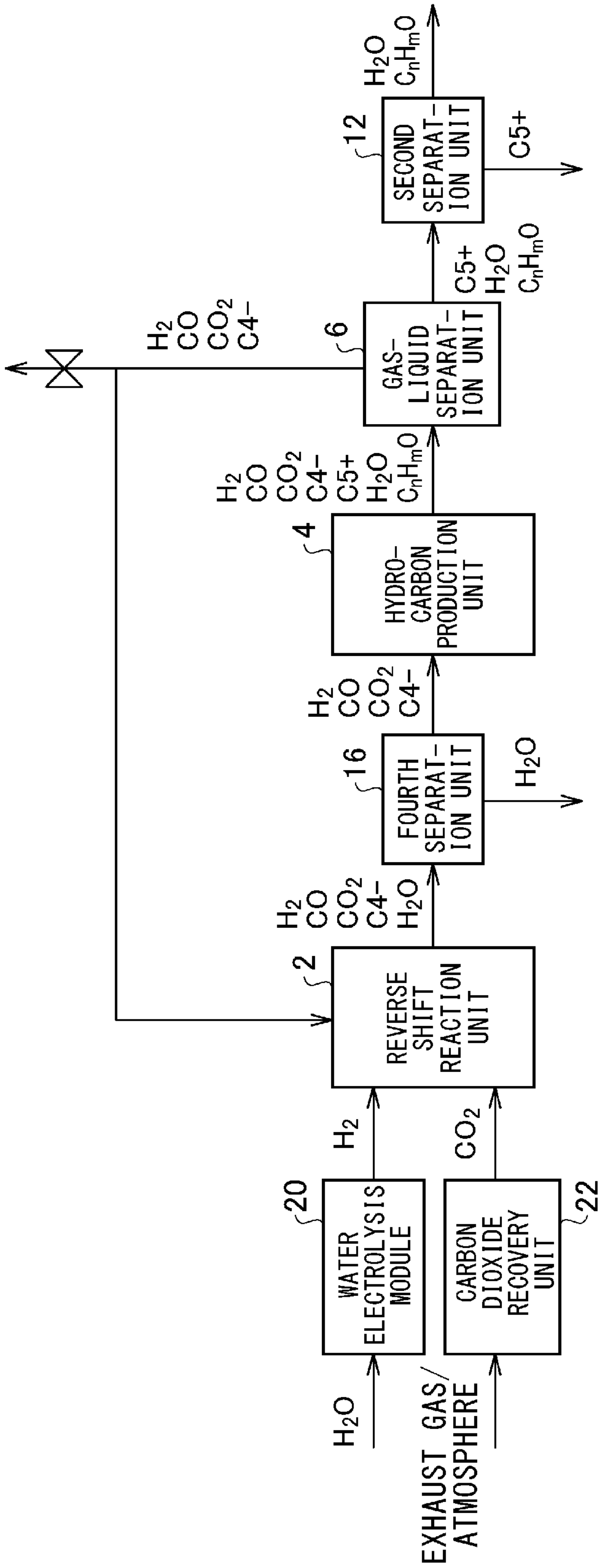
FIG. 2 is a schematic diagram of a hydrocarbon production apparatus according to a comparative example.
Figure 3:
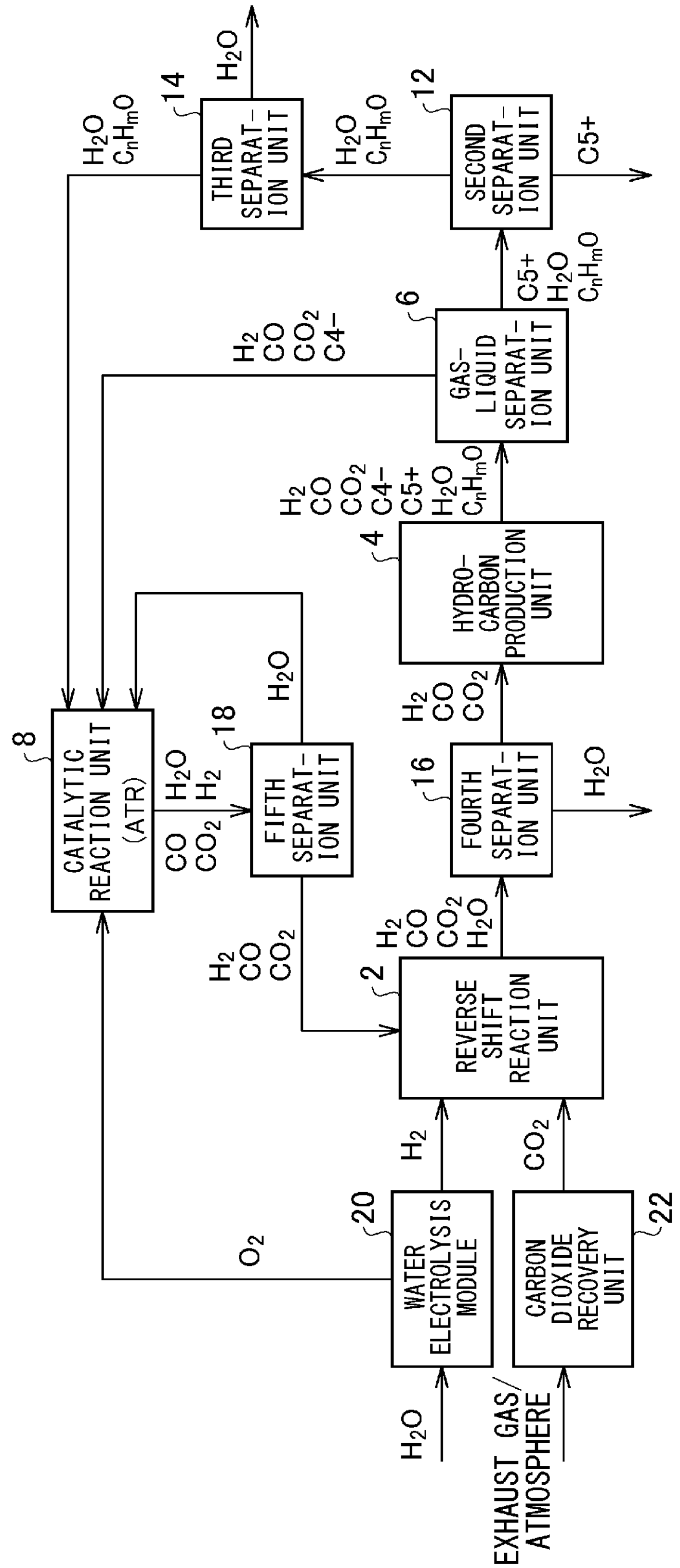
FIG. 3 is a schematic diagram of a hydrocarbon production apparatus according to Test Example 1.
Figure 4:
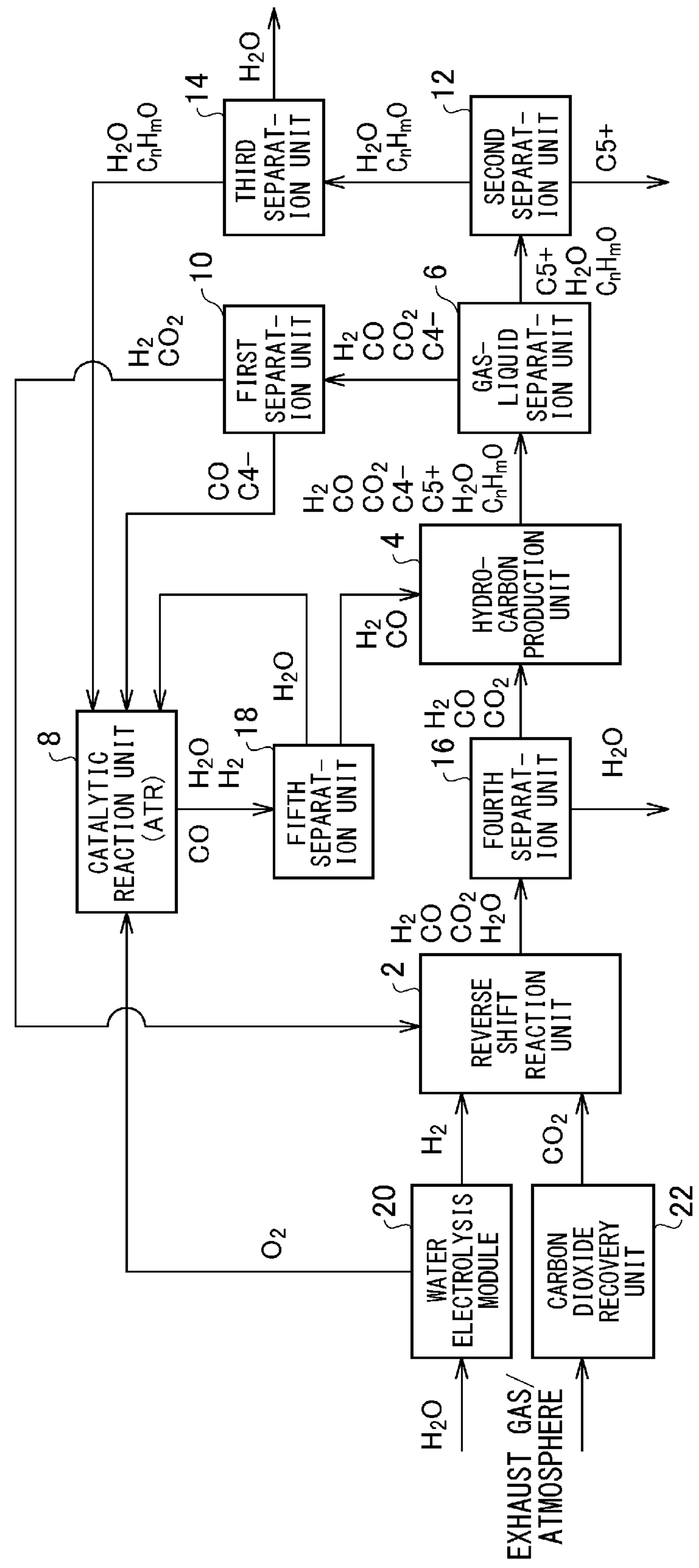
FIG. 4 is a schematic diagram of a hydrocarbon production apparatus according to Test Example 2.
Figure 5:
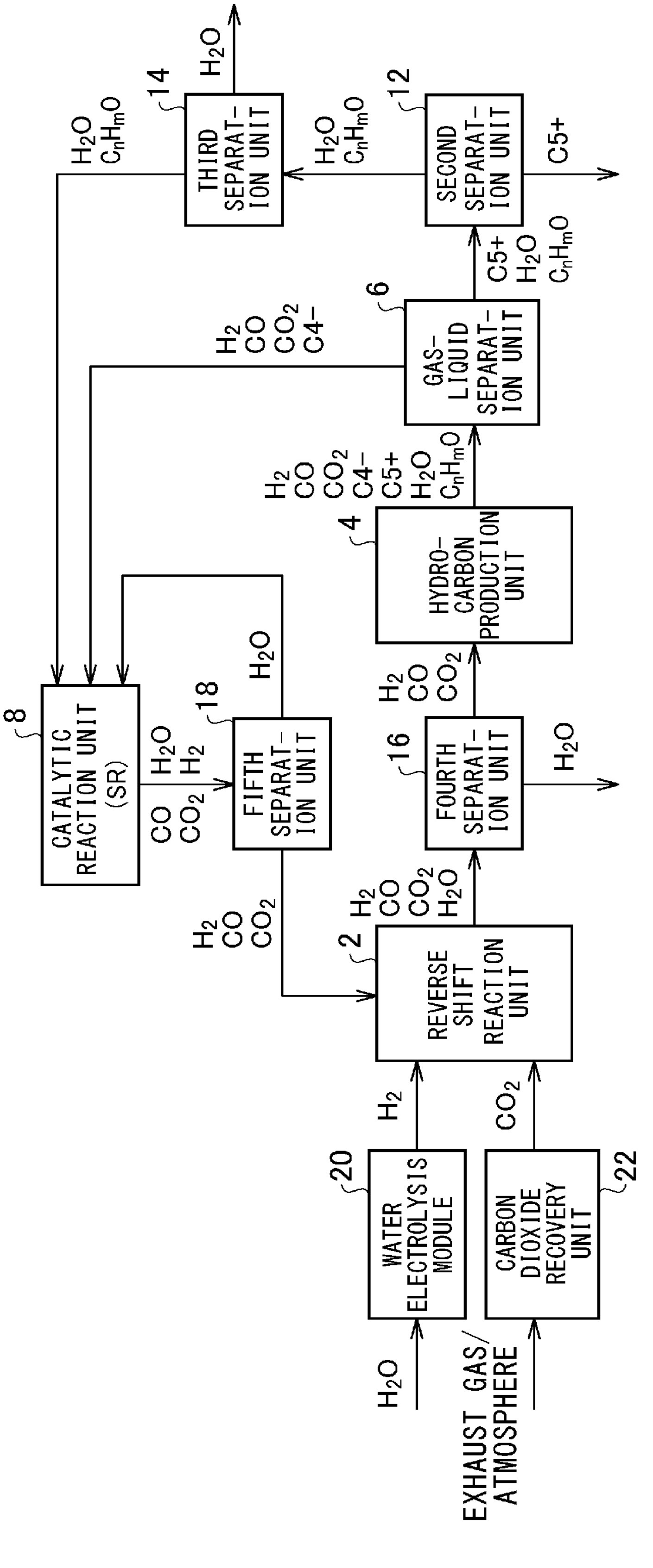
FIG. 5 is a schematic diagram of a hydrocarbon production apparatus according to Test Example 3.
Figure 6:
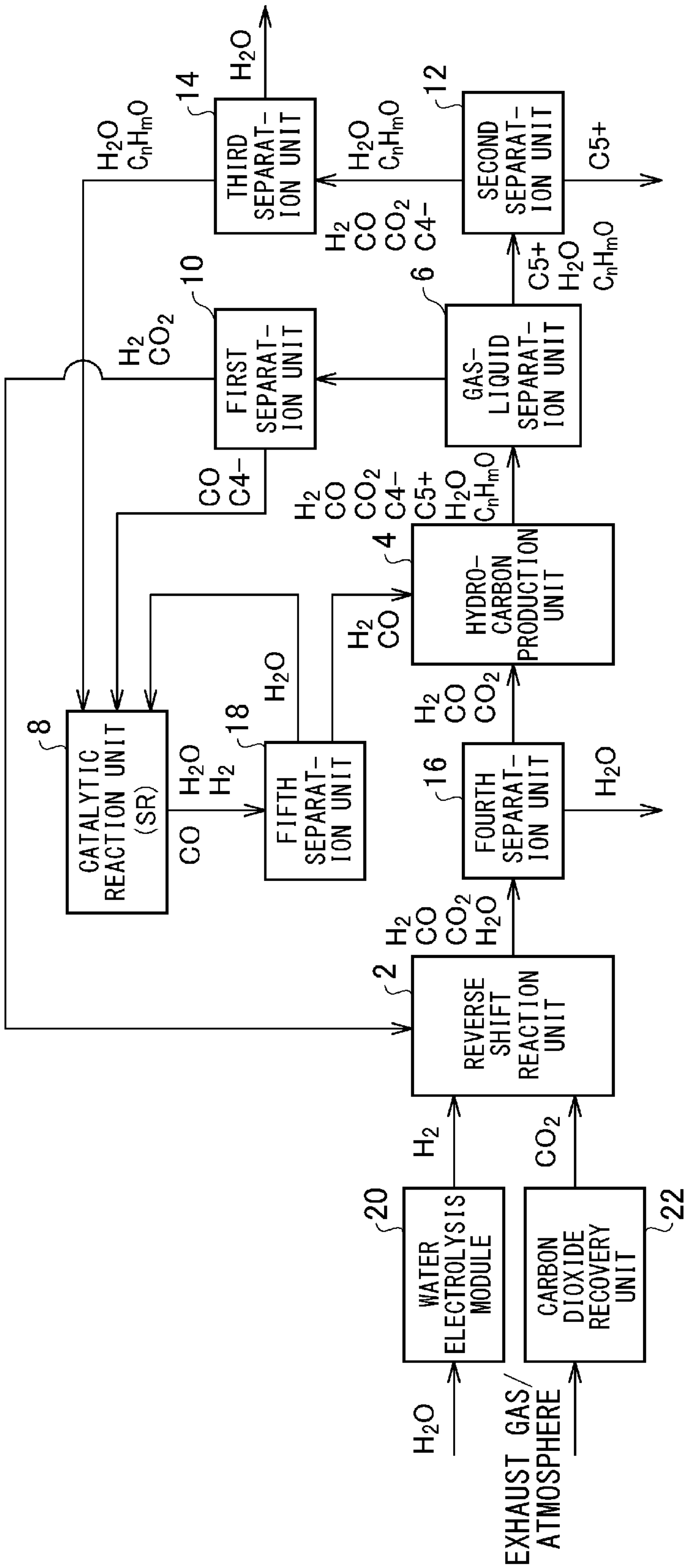
FIG. 6 is a schematic diagram of a hydrocarbon production apparatus according to Test Example 4.

Hereinafter, the operation of the hydrocarbon production apparatus 1 according to the present embodiment will be verified. FIG. 2 is a schematic diagram of a hydrocarbon production apparatus according to a comparative example. FIG. 3 is a schematic diagram of a hydrocarbon production apparatus according to Test Example 1. FIG. 4 is a schematic diagram of a hydrocarbon production apparatus according to Test Example 2. FIG. 5 is a schematic diagram of a hydrocarbon production apparatus according to Test Example 3. FIG. 6 is a schematic diagram of a hydrocarbon production apparatus according to Test Example 4.

As illustrated in FIG. 2, the hydrocarbon production apparatus according to the comparative example does not include the catalytic reaction unit 8 and the first separation unit 10. Therefore, the gas component separated by the gas-liquid separation unit 6 is directly recycled to the reverse shift reaction unit 2. The third separation unit 14 is also not provided. Therefore, separation of water from the aqueous component separated by the second separation unit 12, that is, a concentration treatment of the oxygenated hydrocarbon is not performed.

As illustrated in FIG. 3, the hydrocarbon production apparatus according to Test Example 1 does not include the first separation unit 10. Therefore, the gas component separated by the gas-liquid separation unit 6 is directly recycled to the catalytic reaction unit 8. The catalytic reaction unit 8 is constituted by an autothermal reformer (ATR). The hydrogen, carbon monoxide, and carbon dioxide separated by the fifth separation unit 18 are recycled to the reverse shift reaction unit 2. The third separation unit 14 is provided. Therefore, the aqueous component separated by the second separation unit 12 is subjected to a concentration treatment of the oxygenated hydrocarbon. The water in which the oxygenated hydrocarbon is concentrated is recycled to the catalytic reaction unit 8.

As illustrated in FIG. 4, the hydrocarbon production apparatus according to Test Example 2 includes the first separation unit 10. The C4− component and carbon monoxide separated by the first separation unit 10 are recycled to the catalytic reaction unit 8. The hydrogen and carbon dioxide separated by the first separation unit 10 are recycled to the reverse shift reaction unit 2. The catalytic reaction unit 8 is constituted by an autothermal reformer. The hydrogen and carbon monoxide separated by the fifth separation unit 18 are recycled to the hydrocarbon production unit 4. The third separation unit 14 is also provided. Therefore, the aqueous component separated by the second separation unit 12 is subjected to a concentration treatment of the oxygenated hydrocarbon. The water in which the oxygenated hydrocarbon is concentrated is recycled to the catalytic reaction unit 8.

As illustrated in FIG. 5, the hydrocarbon production apparatus according to Test Example 3 does not include the first separation unit 10. Therefore, the gas component separated by the gas-liquid separation unit 6 is directly recycled to the catalytic reaction unit 8. The catalytic reaction unit 8 is constituted by a steam reformer (SR). The hydrogen, carbon monoxide, and carbon dioxide separated by the fifth separation unit 18 are recycled to the reverse shift reaction unit 2. The third separation unit 14 is provided. Therefore, the aqueous component separated by the second separation unit 12 is subjected to a concentration treatment of the oxygenated hydrocarbon. The water in which the oxygenated hydrocarbon is concentrated is recycled to the catalytic reaction unit 8.

As illustrated in FIG. 6, the hydrocarbon production apparatus according to Test Example 4 includes the first separation unit 10. The C4− component and carbon monoxide separated by the first separation unit 10 are recycled to the catalytic reaction unit 8. The hydrogen and carbon dioxide separated by the first separation unit 10 are recycled to the reverse shift reaction unit 2. The catalytic reaction unit 8 is constituted by a steam reformer. The hydrogen and carbon monoxide separated by the fifth separation unit 18 are recycled to the hydrocarbon production unit 4. The third separation unit 14 is also provided. Therefore, the aqueous component separated by the second separation unit 12 is subjected to a concentration treatment of the oxygenated hydrocarbon. The water in which the oxygenated hydrocarbon is concentrated is recycled to the catalytic reaction unit 8.

A C5+ component was produced under predetermined conditions by using the hydrocarbon production apparatuses of the comparative example and each Test Example. The energy efficiency (see Formula (20)) at that time was calculated. The reaction conditions at the time of calculating the energy efficiency were as follows. In addition to the following reaction conditions, the $H_2/CO_2$ ratio of the fresh feed was adjusted so that the $H_2/CO_2$ ratio (molar ratio) to be supplied to the reverse shift reaction unit maintained 3. Except for the FT reaction in the hydrocarbon production unit, each reaction was allowed to proceed until the equilibrium composition was achieved.

Reaction temperature of reverse shift reaction unit: 800° C.

Reaction temperature of hydrocarbon production unit: 200° C.

Reaction temperature of autothermal reformer or steam reformer: 880° C.

Reaction pressure (constant in the system): 4 MPa

The energy efficiency in each Test Example when the energy efficiency in the comparative example was regarded as "1" (energy efficiency of Test Example/energy efficiency of comparative example) was compared between a case where recycling of the aqueous component separated by the second separation unit 12 or the water separated by the third separation unit 14 to the water electrolysis module 20 was performed and a case where such recycling was not performed. The results are as follows.

When recycling of the aqueous component was not performed

Comparative Example: 1.00

Test Example 1: 1.05

Test Example 2: 1.17

Test Example 3: 0.99

Test Example 4: 1.19

When recycling of the aqueous component was performed

Comparative Example: 1.00

Test Example 1: 1.03

Test Example 2: 1.13

Test Example 3: 1.12

Test Example 4: 1.34

From the comparison between Test Example 1 and Test Example 2 and the comparison between Test Example 3 and Test Example 4, it was confirmed that the energy efficiency required for the production of the C5+ component can be improved and thus the production efficiency of the C5+ component can be improved by separating hydrogen and carbon dioxide, and a C4− component by the first separation unit 10 and recycling the hydrogen and carbon dioxide to the reverse shift reaction unit 2 and the C4− component to the catalytic reaction unit 8, respectively. The present inventors have confirmed that the $H_2/CO_2$ ratio of the fresh feed can be reduced from about 3 to about 2 by changing the catalytic reaction unit 8 from an autothermal reformer to a steam reformer.

Embodiments may be identified by the items described below.

[Item 1]

A hydrocarbon production apparatus (1) including:

a reverse shift reaction unit (2) structured to reduce carbon dioxide to carbon monoxide by a reverse shift reaction by using carbon dioxide and hydrogen as source gases to obtain a synthesis gas containing carbon monoxide and hydrogen;

a hydrocarbon production unit (4) structured to produce a hydrocarbon by using the synthesis gas;

a gas-liquid separation unit (6) structured to separate a gas component containing hydrogen, carbon dioxide, and a light hydrocarbon (C4−) having 4 or less carbon atoms and a liquid component containing a hydrocarbon having 5 or more carbon atoms (C5+) from an effluent from the hydrocarbon production unit (4);

a first separation unit (10) structured to separate hydrogen and carbon dioxide, and a light hydrocarbon (C4−) from the gas component; and a catalytic reaction unit (8) structured to receive supply of the light hydrocarbon (C4−) separated by the first separation unit (10) to generate hydrogen and carbon monoxide by using the light hydrocarbon (C4−), wherein the reverse shift reaction unit (2) is structured to receive supply of the hydrogen and carbon dioxide separated by the first separation unit (10) and also use the hydrogen and carbon dioxide for generation of the synthesis gas, and the hydrocarbon production unit (4) is structured to receive supply of the hydrogen and carbon monoxide generated by the catalytic reaction unit (8) and also use the hydrogen and carbon monoxide for production of the hydrocarbon.

[Item 2]

The hydrocarbon production apparatus (1) described in Item 1, in which the liquid component contains an oily component containing a hydrocarbon having 5 or more carbon atoms (C5+) and an aqueous component containing water, the catalytic reaction unit (8) is structured to generate hydrogen and carbon monoxide from the light hydrocarbon (C4−) by a reforming reaction, the hydrocarbon production apparatus (1) includes a second separation unit (12) structured to separate an aqueous component from the liquid component, and the catalytic reaction unit (8) is structured to receive supply of the aqueous component separated by the second separation unit (12) and also use the aqueous component for generation of hydrogen and carbon monoxide.

[Item 3]

The hydrocarbon production apparatus (1) described in Item 2, in which the aqueous component also contains a hydrophilic oxygenated hydrocarbon dissolved in water, the hydrocarbon production apparatus (1) includes a third separation unit (14) structured to separate at least a part of water from the aqueous component, and the catalytic reaction unit (8) is structured to receive supply of the aqueous component from which water is separated by the third separation unit (14) and use the aqueous component for generation of hydrogen and carbon monoxide.

[Item 4]

The hydrocarbon production apparatus (1) described in any one of Items 1 to 3, in which the catalytic reaction unit (8) is structured to generate methane from the light hydrocarbon (C4−) by a reforming reaction at a first temperature and generate carbon monoxide and hydrogen from the methane by a reforming reaction at a second temperature higher than the first temperature.

[Item 5]

A hydrocarbon production method including:

a reverse shift reaction step of reducing carbon dioxide to carbon monoxide by a reverse shift reaction by using carbon dioxide and hydrogen as source gases to obtain a synthesis gas containing carbon monoxide and hydrogen;

a hydrocarbon production step of producing a hydrocarbon by using the synthesis gas;

a gas-liquid separation step of separating a gas component containing hydrogen, carbon dioxide, and a light hydrocarbon (C4−) having 4 or less carbon atoms and a liquid component containing a hydrocarbon having 5 or more carbon atoms (C5+) from an effluent from the hydrocarbon production step;

a first separation step of separating hydrogen and carbon dioxide, and a light hydrocarbon (C4−) from the gas component; and a catalytic reaction step of receiving supply of the light hydrocarbon (C4−) separated by the first separation step to generate hydrogen and carbon monoxide by using the light hydrocarbon (C4−), wherein in the reverse shift reaction step, supply of the hydrogen and carbon dioxide separated by the first separation step is received and the hydrogen and carbon dioxide are also used for generation of the synthesis gas, and in the hydrocarbon production step, supply of the hydrogen and carbon monoxide generated by the catalytic reaction step is received and the hydrogen and carbon monoxide are also used for production of the hydrocarbon.

[Item 6]

The hydrocarbon production method described in Item 5, in which the liquid component contains an oily component containing a hydrocarbon having 5 or more carbon atoms (C5+) and an aqueous component containing water, in the catalytic reaction step, hydrogen and carbon monoxide are generated from the light hydrocarbon (C4−) by a reforming reaction, the hydrocarbon production method comprises a second separation step of separating an aqueous component from the liquid component, and in the catalytic reaction step, supply of the aqueous component separated by the second separation step is received and the aqueous component is also used for generation of hydrogen and carbon monoxide.

The invention claimed is:

1. A hydrocarbon production apparatus comprising:

a reverse shift reaction unit structured to reduce carbon dioxide to carbon monoxide by a reverse shift reaction by using carbon dioxide and hydrogen as source gases to obtain a synthesis gas containing carbon monoxide and hydrogen;

a hydrocarbon production unit structured to produce a hydrocarbon by using the synthesis gas;

a gas-liquid separation unit structured to separate a gas component containing hydrogen, carbon dioxide, and a light hydrocarbon having 4 or less carbon atoms and a liquid component containing a hydrocarbon having 5 or more carbon atoms from an effluent from the hydrocarbon production unit;

a first separation unit structured to separate hydrogen and carbon dioxide, and a light hydrocarbon from the gas component; and a catalytic reaction unit structured to receive supply of the light hydrocarbon separated by the first separation unit to generate hydrogen and carbon monoxide by using the light hydrocarbon, wherein the reverse shift reaction unit is structured to receive supply of the hydrogen and carbon dioxide separated by the first separation unit and also use the hydrogen and carbon dioxide for generation of the synthesis gas, and the hydrocarbon production unit is structured to receive supply of the hydrogen and carbon monoxide generated by the catalytic reaction unit and also use the hydrogen and carbon monoxide for production of the hydrocarbon.

2. The hydrocarbon production apparatus according to claim 1, wherein the liquid component contains an oily component containing a hydrocarbon having 5 or more carbon atoms and an aqueous component containing water, the catalytic reaction unit is structured to generate hydrogen and carbon monoxide from the light hydrocarbon by a reforming reaction, the hydrocarbon production apparatus comprises a second separation unit structured to separate an aqueous component from the liquid component, and the catalytic reaction unit is structured to receive supply of the aqueous component separated by the second separation unit and also use the aqueous component for generation of hydrogen and carbon monoxide.

3. The hydrocarbon production apparatus according to claim 2, wherein the aqueous component also contains a hydrophilic oxygenated hydrocarbon dissolved in water, the hydrocarbon production apparatus comprises a third separation unit structured to separate at least a part of water from the aqueous component, and the catalytic reaction unit is structured to receive supply of the aqueous component from which water is separated by the third separation unit and use the aqueous component for generation of hydrogen and carbon monoxide.

4. The hydrocarbon production apparatus according to claim 1, wherein the catalytic reaction unit is structured to generate methane from the light hydrocarbon by a reforming reaction at a first temperature and generate carbon monoxide and hydrogen from the methane by a reforming reaction at a second temperature higher than the first temperature.

5. A hydrocarbon production method comprising:

a reverse shift reaction step of reducing carbon dioxide to carbon monoxide by a reverse shift reaction by using carbon dioxide and hydrogen as source gases to obtain a synthesis gas containing carbon monoxide and hydrogen;

a hydrocarbon production step of producing a hydrocarbon by using the synthesis gas;

a gas-liquid separation step of separating a gas component containing hydrogen, carbon dioxide, and a light hydrocarbon having 4 or less carbon atoms and a liquid component containing a hydrocarbon having 5 or more carbon atoms from an effluent from the hydrocarbon production step;

a first separation step of separating hydrogen and carbon dioxide, and a light hydrocarbon from the gas component; and a catalytic reaction step of receiving supply of the light hydrocarbon separated by the first separation step to generate hydrogen and carbon monoxide by using the light hydrocarbon, wherein in the reverse shift reaction step, supply of the hydrogen and carbon dioxide separated by the first separation step is received and the hydrogen and carbon dioxide are also used for generation of the synthesis gas, and in the hydrocarbon production step, supply of the hydrogen and carbon monoxide generated by the catalytic reaction step is received and the hydrogen and carbon monoxide are also used for production of the hydrocarbon.

6. The hydrocarbon production method according to claim 5, wherein the liquid component contains an oily component containing a hydrocarbon having 5 or more carbon atoms and an aqueous component containing water, in the catalytic reaction step, hydrogen and carbon monoxide are generated from the light hydrocarbon by a reforming reaction, the hydrocarbon production method comprises a second separation step of separating an aqueous component from the liquid component, and in the catalytic reaction step, supply of the aqueous component separated by the second separation step is received and the aqueous component is also used for generation of hydrogen and carbon monoxide.

* * * * *